(12) United States Patent
Stamm et al.

(10) Patent No.: US 6,433,224 B1
(45) Date of Patent: Aug. 13, 2002

(54) METHOD FOR PRODUCING CARBOXYLIC ACID CHLORIDES

(75) Inventors: Armin Stamm, Mainz; Jochem Henkelmann, Mannheim, both of (DE)

(73) Assignee: BASF Aktiengesellschaft, Lidwigshafen (DE)

( * ) Notice: Subject to any disclaimer, the term of this patent is extended or adjusted under 35 U.S.C. 154(b) by 0 days.

(21) Appl. No.: 09/830,347

(22) PCT Filed: Oct. 29, 1999

(86) PCT No.: PCT/EP99/08214

§ 371 (c)(1),
(2), (4) Date: Apr. 25, 2001

(87) PCT Pub. No.: WO00/26171

PCT Pub. Date: May 11, 2000

(30) Foreign Application Priority Data

Nov. 4, 1998 (DE) .......................................... 198 50 857

(51) Int. Cl.⁷ ............................................... C07C 51/58

(52) U.S. Cl. ....................................................... 562/857
(58) Field of Search .......................................... 562/857

(56) References Cited

U.S. PATENT DOCUMENTS

| 3,492,331 A | 1/1970 | Sayigh |
| 3,547,960 A | 12/1970 | Hauser |

FOREIGN PATENT DOCUMENTS

| EP | 213 976 | 3/1987 |
| EP | 531 826 | 3/1993 |

*Primary Examiner*—Paul J. Killos
(74) *Attorney, Agent, or Firm*—Keil & Weinkauf

(57) ABSTRACT

The invention relates to a process for the preparation of acid chlorides by reaction of carboxylic acids, carboxylic anhydrides, cyclic carboxylic esters or sulfonic acids with phosgene in the presence of a catalytic amount of a compound from the group consisting of N,N,N',N'-tetrasubstituted amidinium halides (I), N,N,N'-trisubstituted amidinium hydrohalides (II) and N,N,N'-trisubstituted amidines (III).

6 Claims, No Drawings

METHOD FOR PRODUCING CARBOXYLIC ACID CHLORIDES

The present invention relates to a process for the preparation of carbonyl chlorides from carboxylic acids, carboxylic anhydrides, cyclic carboxylic esters (lactones) or sulfonic acids.

Carbonyl chlorides are important reactive intermediates in the preparation of fibers, films and in pharmaceutical chemistry and agrochemistry. Thus, a number of preparation processes for the synthesis of carbonyl chlorides from carboxylic acids or carboxylic anhydrides is known. In the industrial preparation, it is possible to differentiate between three methods for the preparation of carbonyl chlorides:

1. the chlorination of carboxylic acids or carboxylic anhydrides with phosphorus trichloride,
2. the chlorination of carboxylic acids or carboxylic anhydrides with thionyl chloride,
3. the chlorination of carboxylic acids or carboxylic anhydrides with phosgene.

The chlorination with phosgene is advantageous as compared with the other processes since only gaseous by-products form, which can be removed easily by expulsion with, for example, nitrogen. In contrast to thionyl chloride, toxic $SO_2$ is not formed, but rather nontoxic $CO_2$. Furthermore, phosgene is a low-cost chlorinating agent. The chlorination with phosgene is therefore a very economical route for the preparation of carbonyl chloride.

Since phosgene on its own is too unreactive at suitable reaction temperatures and pressures, the use of a catalyst is necessary.

The literature describes a number of processes in which N,N-disubstituted formamides or their hydrochlorides are used as phosgenation catalysts. These react with phosgene to give so-called Vilsmeier salts. The Vilsmeier salt, the actual reactive chlorinating reagent, reacts with a carboxylic acid or a carboxylic anhydride to give the acid chloride. In the reaction, formamide hydrochloride is reformed, which in turn can react with phosgene to give the Vilsmeier salt, and passes through further catalyst cycles. The N,N-disubstituted formamide hydrochlorides or their Vilsmeier salts are, however, not entirely thermally stable, meaning that temperatures above from 80 to 90° C. can lead to secondary reactions.

EP-A 0 213 976 describes the use of hexaalkylguanidinium salts as catalysts. These need only be added to the reaction mixture in small amounts to achieve adequate selectivity. A disadvantage of this class of compound is, however, its complex preparation.

U.S. Pat. No. 3,547,960 discloses the use of certain catalysts which have C—N or N—N double bonds. Inter alia, cyclic amidines are disclosed as catalysts. Preferred catalysts are imidazoles or hydrochloride salts thereof and triazoles.

It is an object of the present invention to provide catalysts for the reaction of carboxylic acids, carboxylic anhydrides, cyclic carboxylic esters (lactones) or sulfonic acids with phosgene to give carbonyl chlorides which can be prepared more readily than known catalysts and can be used for a large number of compounds. Furthermore, the catalysts should permit shorter reaction times than the catalysts known hitherto and very good conversions.

We have found that this object is achieved by a process for the preparation of acid chlorides by reaction of carboxylic acids, carboxylic anhydrides, cyclic carboxylic esters (lactones) or sulfonic acids with phosgene in the presence of a catalytic amount of a compound from the group consisting of N,N,N',N'-tetrasubstituted amidinium halides (I), N,N,N'-trisubstituted amidinium hydrohalides (II) and N,N,N'-trisubstituted amidines (III) of the formula

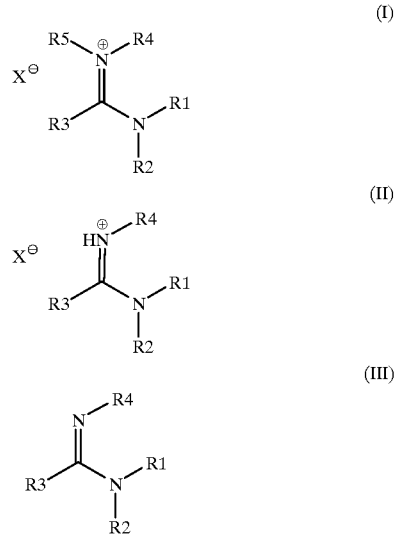

in which $R^1$, $R^2$ and $R^4$ are linear or branched alkyl chains having a length of from 1 to 20 carbon atoms or cycloaliphatic radicals having a ring size of from 5 to 8 carbon atoms, where the rings can be interrupted by heteroatoms, or $R^1$ and $R^2$ are unsubstituted or substituted aromatic radicals or together form a chain of four or five methylene groups;

$R^3$ is a hydrogen atom or a branched or unbranched alkyl radical or a cycloalkyl radical having a length of from 1 to 6 carbon atoms; and R5 in compound I is a branched or unbranched $C_1$ to $C_6$-alkyl chain, and $X^-$ is a halide.

Thus, $R^1$, $R^2$ and $R^4$, and also $R^5$, can, for example, independently of one another be alkyl radicals such as methyl, ethyl, n-propyl, isopropyl, n-butyl, isobutyl, tert-butyl or linear or branched pentyl radicals. The radicals $R^1$, $R^2$ and $R^4$ can also be cycloalkyl radicals, such as cyclopentyl and cyclohexyl radicals, and $R^1$ and $R^2$ can be aromatic radicals, substituted or unsubstituted, such as phenyl and tolyl radicals.

$R^3$ can, for example, be the same alkyl radicals as listed for $R^1$, $R^2$, $R^4$ and $R^5$. Preferably, however, $R^3$ is hydrogen. $X^-$ is preferably bromide or chloride, very particularly preferably chloride.

Particularly preferably, the radicals $R^1$, $R^2$, $R^4$ and $R^5$ are methyl or ethyl radicals, and $R^3$ is hydrogen. Particular preference is given to N,N,N'-trimethy-formamidine ($R^1$=$R^2$=$R^4$=methyl, $R^3$=H), N,N,N'-trimethylformamidine hydrochloride ($R^1$=$R^2$=$R^4$=methyl, $R^3$=H),N,N,N',N'tetramethylformamidinium chloride ($R^1$=$R^2$=$R^4$=$R^5$=methyl, $R^3$=H) and N,N-diethyl-N',N'-dimethylformamidinium hydrochloride ($R^1$=$R^2$=methyl, $R^4$=$R^5$=ethyl, $R^3$=H).

The catalysts used in the process according to the invention are also obtainable on a larger scale by simple reaction. They permit reaction in very good yields and short reaction times.

The N,N,N',N'-tetrasubstituted formamidinium salts (I) ($R^3$=H) are obtainable via a single-stage reaction from formamides with N,N-disubstituted dialkylcarbamoyl halides. A synthesis of the compounds is described in Coll. Czech. Chem. Comm. 24 (1959), 760 to 765. N,N,N'-

Trisubstituted amidinium hydrohalides (II) can be prepared by reaction of N-monosubstituted amides with N,N-dialkylcarbamoyl halides in a single-stage synthesis in accordance with Kantlehner et al., Synthesis 1983. The free amidines (III) can be liberated by neutralization of the resulting amidine hydrohalides using an inorganic base.

Since the preparation of the free amidines (III) requires an additional reaction step, namely the neutralization of the hydrohalides (II), in the process according to the invention preference is given to using the amidinium hydrohalides of the formula II.

In a further preferred embodiment, N,N,N',N'-tetrasubstituted amidinium halides (I), particularly preferably formamidinium halides, are used, which are likewise obtainable via a single-stage reaction, as already described.

The catalytic action of the amidinium salts I and II in the process according to the invention is surprising since they have hitherto been considered to be reaction-inhibiting. For example, U.S. Pat. No. 3,547,960 states that a disadvantage of processes in which carboxamides are used as catalysts is that tarry, catalytically inactive products are formed during this reaction as a result of the decomposition of the carboxamide catalysts. From the literature, however, it is known that formamidinium halides form as decomposition product of the carboxamide DMF (dimethylformamide).

The reactions in which amidines, amidinium hydrohalides and amidinium halides are used are more successful the more substituents the two nitrogen atoms have. The reaction does not proceed to completion if substituents are not present (Comparative Examples 5 and 6). With two substituents on the nitrogen atoms, the reaction proceeds slowly and relatively large amounts of the carboxylic anhydride are formed (Comparative Example 7).

The carboxylic acids which can be used in the process according to the invention are not restricted. In general, use is made of aliphatic carboxylic acids having from 2 to 22 carbon atoms or mixtures of $C_8$–$C_{22}$ carboxylic acids, the radicals of which can be branched or linear, saturated or unsaturated and optionally substituted by, for example, halogen or nitro groups. Furthermore, it is possible to use aromatic and cycloaliphatic carboxylic acids, and aralkyl- or alkylaryl-substituted carboxylic acids having from 7 to 24 carbon atoms. Suitable acids can comprise from one to three carboxyl groups. Suitable aliphatic acids are, for example, pivalic acid, 2-ethylhexanoic acid, stearic acid, butyric acid, lauric acid, palmitic acid, acetic acid, neopentanoic acid, chloroacetic acid, dichloroacetic acid, adipic acid, sebacic acid, acrylic acid, methacrylic acid etc. Suitable aromatic acids are, for example, benzoic acid, m-nitrobenzoic acid, isophthalic acid, phenylacetic acid, p-chlorobenzoic acid, trans-cinnamic acid, m-toluic acid etc. An example of a suitable cycloaliphatic acid is cyclohexanecarboxylic acid.

Suitable carboxylic anhydrides for the process according to the invention are generally anhydrides of the formula (IV)

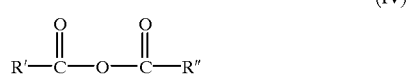

(IV)

in which R' and R" are each an organic radical, for example a hydrocarbon radical. Particularly suitable are carboxylic anhydrides which carry aliphatic groups, which can be branched or linear, saturated or unsaturated and optionally substituted by halogen or nitro groups, or cycloaliphatic or aromatic groups, and aralkyl or alkylaryl groups. Thus, R' or R" can be alkylene, alkenylene, cycloalkylene, arylene or a divalent, saturated or unsaturated group. The number of carbon atoms in the aliphatic radicals R' and R" is preferably from 1 to 24, particularly preferably from 1 to 12, and in aromatic, cycloaliphatic, aralkyl or alkylaryl radicals is from 6 to 24, preferably from 6 to 12. Thus, anhydrides may, for example, be acetic anhydride, butyric anhydride, hexanoic anhydride, benzoic anhydride, trimellitic anhydride, octanoic anhydride, chloroacetic anhydride, acrylic anhydride, phenylacetic anhydride, adipic anhydride, sebacic anhydride, nitrobenzoic anhydride, chlorobenzoic anhydride, toluic anhydride, isophthalic anhydride and terephthalic anhydride.

Suitable cyclic carboxylic esters (lactones) for the process according to the invention are generally cyclic esters of the formula V:

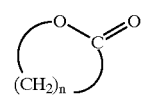

V in which n=2 to 9.

In addition, mono- or polysubstituted cyclic carboxylic esters in which one or both hydrogen atoms of one or more $CH_2$ groups have been replaced by substituents, in particular alkyl groups, are also suitable.

Particular preference is given to unsubstituted cyclic carboxylic esters, very particularly preferably where n=3 to 5. Thus, for example, γ-butyrolactone, δ-valerolactone and ε-caprolactone are suitable.

The catalyst is generally used in the process according to the invention in an amount of from 0.1 to 5 mol %, preferably from 0.5 to 3 mol %, particularly preferably from 1 to 2 mol %, based on the amount of carboxylic acid used, of the carboxylic anhydride used, of the cyclic carboxylic ester used or of the sulfonic acid used.

The process according to the invention can be carried out in the absence or in the presence of an organic solvent which is inert toward phosgene. Preferred solvents are hydrocarbons. Particular preference is given to mono- or polysubstituted aromatic hydrocarbons, very particular preference to toluene, o-, m-, p-xylene or chlorobenzene.

In a particularly preferred variant, in particular during reaction of cyclic carboxylic esters (lactones), the desired carbonyl chloride is used as solvent.

However, the absence of additional solvent is preferred over carrying out the process according to the invention in the presence of a solvent. This avoids separating the solvent off from the reaction product and thus an additional process step.

The process can be carried out in any apparatus suitable for the reaction. Thus, for example, it is possible to use a phosgenation apparatus with attached carbonic acid condenser. In this connection, the process can be carried out discontinuously or continuously, preferably continuously. The reaction temperature in the process according to the invention is dependent on the carboxylic acid used or on the carboxylic anhydride used. Generally, the process according to the invention is carried out at temperatures of from 40 to 150° C., preferably from 60 to 120° C., particularly preferably from 80 to 100° C. The reaction pressure is unimportant for the reaction. For the most part, the reaction is carried out at a pressure of generally from 0.5 to 5 bar, preferably from 0.5 to 2 bar, particularly preferably from 0.8 to 1.2 bar, very particularly preferably at atmospheric pressure.

The reaction times are in the range from 1 to 8 hours, preferably in the range from 2 to 4 hours, depending on the amount and type of starting compound used. The GC yields are generally greater than 90%, preferably greater than 95%, particularly preferably greater than 98%. Here, GC yields are yields determined by gas chromatography. The conversions are usually virtually complete.

The phosgene can be added to the reaction mixture in gaseous form or in condensed form.

In a preferred embodiment, the carboxylic acid or the carboxylic anhydride and the catalyst are initially introduced and heated to the reaction temperature. Phosgene is then gassed in or condensed in until the reaction is complete or until the amount of phosgene gassed in or condensed in corresponds at most to twice the molar amount of carboxylic acid used or of carboxylic anhydride used. In general, for a complete conversion, a total of from 1.0 to 2.0 equivalents, preferably from 1.1 to 1.5 equivalents, based on the molar amount of carboxylic acid used or carboxylic anhydride used, of phosgene are required. The acid chlorides formed can be isolated and worked up using methods known to the person skilled in the art, such as distillation, precipitation and filtration and recrystallization etc. The acid chlorides are preferably separated off by simple decantation from the catalyst, which is insoluble in the acid chloride. Such a work-up is simple and low-cost and the catalyst employed can be reused.

The examples below further illustrate the invention.

EXAMPLES

The percentages given below are GC area %.

Example 1

A phosgenation stirred apparatus, comprising a 500 ml four-necked flask, and an attached high-efficiency condenser (Dimroth condenser cooled at −10° C. by means of a Ministat and downstream carbonic acid condenser) is charged with 144 g (1 mol) of 2-ethylhexanoic acid and 1.28 g of N-tert-butyl-N',N'-dimethylformamidine (Aldrich, 1 mol %), and the mixture is heated to 75° C. Over the course of 2 hours 110 g (1.1 mol) of phosgene are gassed in at an internal temperature of between 75 and 85° C. After a post-reaction time of I hour at 80° C., the excess phosgene is stripped off with nitrogen at 60° C. At complete conversion, the reaction product comprises 98.9 GC area % of 2-ethylhexanoyl chloride and 0.2 GC area % of 2-ethylhexanoic anhydride.

Example 2

Example 1 was repeated using 1 mol % of N,N,N'-trimethylformamidine hydrochloride as catalyst. The phosgenation using 105 g (1.05 mol %) of phosgene is carried out between 80 and 90° C. At complete conversion, the reaction product comprises 98.5% of 2-ethylhexanoyl chloride and 0.6% of 2-ethylhexanoic anhydride.

Example 3

Example 2 was repeated using 1.0 mol % of N,N,N',N'-tetramethylformamidinium chloride as catalyst. The reaction was carried out between 80 and 90° C. At complete conversion, the reaction product comprises 98.9% of 2-ethylhexanoyl chloride and 0.4% of 2-ethylhexanoic anhydride.

Example 4

Example 3 was repeated using 1.0 mol % of N,N-dimethyl-N',N'-diethylformamidinium chloride as catalyst.

At complete conversion, the reaction product comprises 98.7% of 2-ethylhexanoyl chloride and 0.2% of 2-ethylhexanoic anhydride.

Example 5

Comparative Example Using Unsubstituted Amidine Hydrochloride

Example 4 was repeated using 1.0 mol % of benzamidine hydrochloride as catalyst. The reaction product comprises 44.8% of unreacted 2-ethylhexanoic acid, 19.7% of 2-ethylhexanoyl chloride and 35.3% of 2-ethylhexanoic anhydride.

Example 6

Comparative Example Using Unsubstituted Amidine Hydrochloride

Example 5 was repeated using 1.0 mol % of acetamidine hydrochloride as catalyst. The reaction product comprises 22.2% of unreacted 2-ethylhexanoic acid, 25.8% of 2-ethylhexanoyl chloride and 51% of 2-ethylhexanoic anhydride.

Example 7

Comparative Example Using a Disubstituted Amidine

Example 6 was repeated using 1.0 mol % of N,N'-diphenylformamidine as catalyst. The reaction product comprises 70.2% of 2-ethylhexanoyl chloride and 28.3% of 2-ethylhexanoic anhydride.

Example 8

Phosgenation of a Cyclic Ester (Discontinuous Procedure)

A phosgenation stirred apparatus comprising a 500 ml four-necked flask and an attached high-efficiency cooling system (Dimroth condenser, cooled at −10° C. with downstream carbonic acid condenser, −78° C.) is charged with 129 g (1.5 mol) of γ-butyrolactone and 4.1 g (0.03 mol) of tetramethylformamidinium chloride (TMFCl), and the mixture is heated to 145° C. Over the course of 4 h, a total of 181 g (1.8 mol) of phosgene and about 40 g (10 g/h) of HCl are introduced into the solution in parallel such that the reaction temperature can be maintained at between 145 and 150° C. After a post-reaction time of 1 h at 145° C., the excess phosgene is stripped off with nitrogen at 80° C. According to gas chromatographic analysis, the reaction product comprises 89.1 area % of 4-chlorobutyryl chloride and 5.0 area % of γ-butyrolactone.

Example 9

Phosgenation of a Cyclic Ester (Semicontinuous Procedure)

A phosgenation stirred apparatus comprising a 500 ml four-necked flask and an attached high-efficiency cooling system (Dimroth condenser, cooled at −10° C., with downstream carbonic acid condenser, −78° C.) is charged with 30 g (0.21 mol) of chlorobutyryl chloride and 0.6 g (0.0042 mol) of tetramethylformamidinium chloride (TMFCl), and the mixture is heated to 145° C. At an internal temperature of from 145 to 150° C. and over 6 h, 10 g/h of hydrogen chloride gas and 28 g/h (0.33 mol/h) of γ-butyrolactone (to which 0.9 g (=2 mol %) of TMFCl has been added), and a total of 156 g (1.56 mol) of phosgene are introduced such that constant phosgene reflux is maintained. When the addition is complete, a further 38 g of phosgene are introduced at from 145 to 150° C. for the post-reaction. After the mixture has been cooled to 80° C., excess phosgene is stripped off with nitrogen. According to gas chromatographic analysis, the reaction product (284 g) comprises 87.8 area % of 4-chlorobutyryl chloride and 6.2 area % of γ-butyrolactone.

We claim:

1. A process for the preparation of acid chlorides by reaction of carboxylic acids, carboxylic anhydrides, cyclic carboxylic esters or sulfonic acids with phosgene in the presence of a catalytic amount of a compound from the group consisting of N,N,N',N'-tetrasubstituted amidinium halides (I), N,N,N'-trisubstituted amidinium hydrohalides (II) and N,N,N'-trisubstituted amidines (III) of the formula

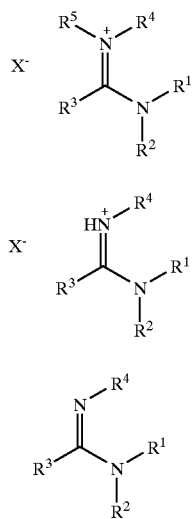

in which the radicals $R^1$, $R^2$ and $R^4$ are linear or branched alkyl chains having from 1 to 20 carbon atoms or cycloaliphatic radicals having a ring size of from 5 to 8 carbon atoms, where the rings can be interrupted by heteroatoms, or $R^1$ and $R^2$ are unsubstituted or substituted aromatic radicals or together form a chain of 4 or 5 methylene groups;

$R^3$ is a hydrogen atom or a branched or unbranched alkyl radical having from 1 to 6 carbon atoms or a cycloalkyl radical having from 3 to 6 carbon atoms and $R^1$ in compound I is a branched or unbranched alkyl chain having from to 6 carbon atoms, and X is a halide.

2. A process as claimed in claim 1, wherein the radicals $R^1$, $R^2$, $R^4$ and $R^1$ in compound I are independently of one another methyl or ethyl groups, and the radical $R^1$ is hydrogen.

3. A process as claimed in claim 2, wherein a catalytic amount of a compound chosen from N,N,N'-trimethylformamidine, N,N,N'-trimethylformamidine hydrochloride, N,N,N',N'-tetramethylformamidinium hydrochloride and N,N-diethyl-N',N'-dimethylformamidinium hydrochloride is used.

4. A process as claimed in claim 1, wherein the catalytic amount is from 0.5 to 5 mol %, based on the amount of carboxylic acid, of carboxylic anhydride, of cyclic carboxylic ester or of sulfonic acid used.

5. A process as claimed in claim 1, wherein the process is carried out in the absence of a solvent or with the desired carbonyl chloride as solvent.

6. A process as claimed in claim 1, wherein the process is carried out at a temperature of from 40 to 120° C.

\* \* \* \* \*

UNITED STATES PATENT AND TRADEMARK OFFICE
CERTIFICATE OF CORRECTION

PATENT NO. : 6,433,224 B1
DATED : August 13, 2002
INVENTOR(S) : Stamm et al.

It is certified that error appears in the above-identified patent and that said Letters Patent is hereby corrected as shown below:

Column 8,
Line 12, "2 to 6" should read -- 1 to 6 --;
Line 14, "$R^1$" should read -- $R^6$ --;
Line 15, "from to 6" should read -- from 1 to 6 --;
Line 17, "X is" should read -- $X^-$ is --.
Line 20, "$R^1$" should read -- $R^3$ --.

Signed and Sealed this

Twenty-first Day of January, 2003

JAMES E. ROGAN
*Director of the United States Patent and Trademark Office*